United States Patent [19]
Peter et al.

[11] 3,933,786
[45] Jan. 20, 1976

[54] HETEROCYCLIC-AZO-PHENYL COMPOUNDS CONTAINING A STYRL GROUP

[75] Inventors: Richard Peter; Hans-Joerg Angliker, both of Basel, Switzerland

[73] Assignee: Ciba-Geigy AG, Basel, Switzerland

[22] Filed: Nov. 20, 1972

[21] Appl. No.: 308,211

Related U.S. Application Data
[62] Division of Ser. No. 56,954, July 21, 1970, Pat. No. 3,717,625.

[30] Foreign Application Priority Data
Aug. 5, 1969  Switzerland.................. 11883/69

[52] U.S. Cl. ............ 260/156; 260/155; 260/157; 260/158; 260/162
[51] Int. Cl.² .......................................... C09B 29/00
[58] Field of Search .......... 260/158, 152, 155, 156, 260/157, 162, 163

[56] References Cited
UNITED STATES PATENTS

| | | |
|---|---|---|
| 2,824,096 | 2/1958 | Heckert.................. 260/206 X |
| 3,069,408 | 12/1962 | Merian et al. .................. 260/158 |
| 3,097,198 | 7/1963 | Fishwick et al............... 260/207.1 |
| 3,190,861 | 6/1965 | Fertig et al. ............. 260/207 X |
| 3,337,522 | 8/1967 | Wegmuller...................... 260/158 |
| 3,518,244 | 6/1970 | Mundlos et al................... 260/149 |
| 3,542,758 | 11/1970 | Hegar ................... 260/156 |
| 3,717,625 | 2/1973 | Peter et al. ............. 260/158 X |

*Primary Examiner*—Charles F. Warren
*Attorney, Agent, or Firm*—Joseph G. Kolodny; Edward McC. Roberts; Prabodh I. Almaula

[57] ABSTRACT

An azo dyestuff that contains at least one residue of a styryl dyestuff. The dyestuffs dye synthetic fibers in bright colours the dyestuffs are of the formula

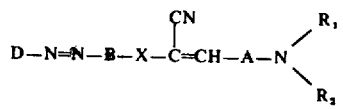

wherein D is a heterocyclic diazo component, B is a coupling component, A is a para-phenylene and $R_1$ and $R_2$ are alkyl that may be substituted.

14 Claims, No Drawings

HETEROCYCLIC-AZO-PHENYL COMPOUNDS CONTAINING A STYRL GROUP

This application is a Division of copending prior application Ser. No. 56,954, filed On July 21, 1970 and now U.S. Pat. No. 3,717,625, issued Feb. 20, 1973.

This invention relates to azo dyestuffs that contain at least one residue of a styryl dyestuff, and especially those dyestuffs that do not contain sulphonic acid groups.

The new dyestuffs may be obtained, for example, when a coupling component that contains a residue of the formula $-CO-CH_2-CN$ a. is condensed with a para-aminobenzaldehyde that may be N,N-dialkylated and
b. coupled with a diazonium compound of a diazo component, the operations being carried out in any desired sequence.

The dyestuffs of the invention may be, for example, azo dyestuffs of the formula

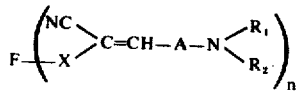

in which X represents a sulphone, carboxylic acid ester or carboxylic acid amide residue, $n = 1$ or 2, the residues $R_1$ and $R_2$ are alkyl residues that may be substituted, and $R_1$ may form a tetramethylene chain bound in ortho-position with the residue A, A represents a para-phenylene residue that may be substituted and F represents the residue of an azo dyestuff that is free from sulphonic acid groups.

Dyestuffs that may be specially mentioned are those of the formula

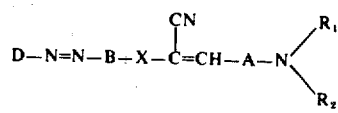

in which D represents the residue of a diazo component, B represents the residue of a coupling component and X, A, $R_1$ and $R_2$ have the meanings given above, and especially the dyestuffs of the formula

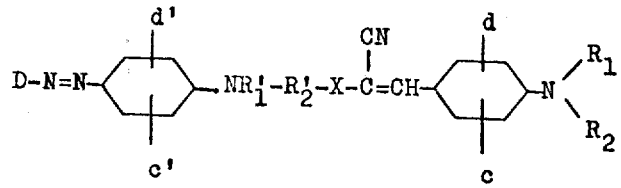

in which $c$, $d$ and $d'$ each represents a hydrogen or a chlorine atom, a lower alkyl group or a lower alkoxy group or a phenyl, phenoxy or phenylthio group, $c'$ is the same as $c$, $d$ or $d'$ or represents a bromine atom, a trifluoromethyl group or an acylamino group, $R_1'$ represents an optionally substituted alkyl residue that may form a tetramethylene chain bound to the benzene residue in ortho-position, $R_2'$ represents an optionally substituted alkylene residue that may be interrupted by hetero atoms and $R_1$, $R_2$, X and D have the meanings given above. The dyestuffs may be further represented by

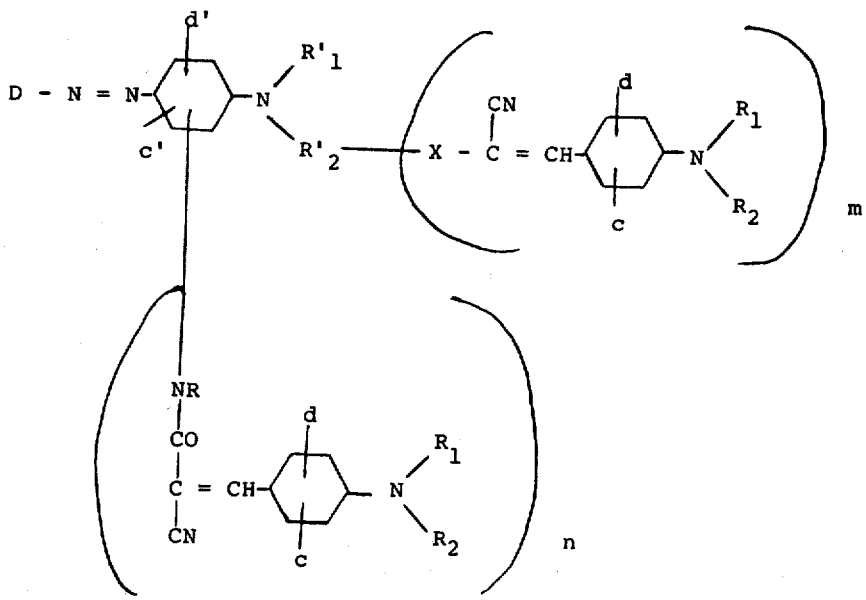

wherein X is phenylene—$SO_2$—, —OCO—, —N($CH_2C_6H_5$)— or -N($C_1$—$C_2$-alkyl)-—CO—, $c$, $d$ and $d'$ each is hydrogen, chlorine, $C_1$-$C_2$-alkyl, $C_1$-$C_2$-alkoxy, phenyl, phenoxy or phenylthio, $c'$ is the same as $c$, $d$ or $d'$ or is bromine, trifluoromethyl, $C_{1-10}$-hydrocarbylcarbonylamino, $C_{1-6}$-hydrocarbylsulfonylamino, $C_{1-8}$-hydrocarbyloxycarbonylamino or $C_{1-8}$-hydrocarbylaminocarbonylamino, each of said hydrocarbyl moieties being aryl or saturated acyclic hydrocarbyl, R is hydrogen or $C_{1-2}$-alkyl, $R_1$, $R_2$, $R'_1$ and $R'_2$ each are, independently, unsubstituted $C_1$-$C_5$-alkyl residue that may form a trimethylene chain bound to the benzene residue in ortho-position, or $C_1$-$C_5$-alkyl optionally interrupted by oxygen and substituted by chlorine, fluorine, hydroxy of $C_1$-$C_5$-alkyl, $C_1$-$C_5$-alkoxy, $C_1$-$C_5$-alkylcarbonyloxy, cyano, bromine, phenyl, phenoxy, phenylmercapto, dichlorophenylmercapto, methoxycarbonyl-thienyl-2-carbonyloxy, trifluoromethyl, benzoyloxy-, methoxycarbonyl-benzoyloxy, methoxybenzoyloxy, $C_1$-$C_5$-alkylaminocarbonyloxy, phenylaminocarbonyloxy, $C_1$-$C_5$-alkylaminocarbonylamino, $C_1$-$C_5$-alkyloxycarbonyloxy or $C_1$-$C_5$-alkoxycarbonyl, m and n are each 0 or 1, only one of said m and n being zero at any one time and D is a diazo component of the heterocyclic series.

Also valuable are the dyestuffs of the formula

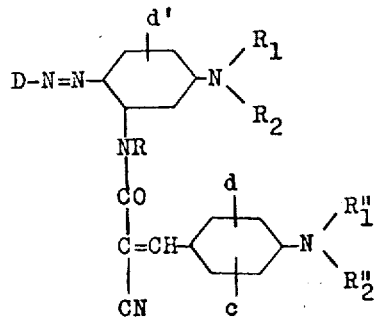

which are obtainable by condensation of a cyanoacetic acid amide of the formula

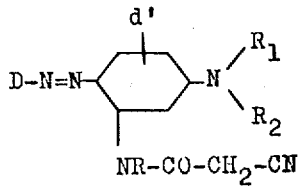

with a para-aminobenzaldehyde of the formula

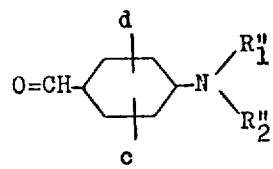

in which D, $R_1$, $R_2$, c, d and d' have the meanings given above, $R_1''$ and $R_2''$ have the same meanings as $R_1$ and $R_2$ and R represents a lower alkyl residue, especially a methyl or ethyl group, or is preferably a hydrogen atom. The residues c, d and d' each represents a hydrogen or chlorine atom, a lower alkyl or alkoxy residue, for example, a methyl, ethyl, methoxy or ethoxy residue, or a phenylthio or phenoxy residue.

The residue c' can have the same meaning as c and also stand for a bromine atom, a trifluoromethyl group and an acylamino group that may be alkylated, preferably methylated, at the nitrogen atom and in which the acyl residue is the residue of a lower carboxylic acid, for example, a formyl, acetyl, propionyl, butyryl or benzoyl residue, the residue of an organic monosulphonic acid, for example, a methane-, ethane- or para-toluenemonosulphonic acid residue, or the residue of a carbonic acid monoester or monamide, for example, a methoxycarbonyl, phenoxycarbonyl, aminocarbonyl or butylaminocarbonyl residue.

The groups $R_1$, $R_2$ and $R_1'$ can be identical or different and can each represent a hydrogen atom, an alkyl or substituted alkyl group, for example, a halogenated alkyl group, for example, a β-chloroethyl, β,β,β-trifluoroethyl, β,γ-dichloropropyl, benzyl, β-phenylethyl or β-cyanoethyl group; an alkoxyalkyl group, for example a β-ethoxyethyl or δ-methoxybutyl group; a hydroxyalkyl group, for example, a β-hydroxyethyl or β,γ-dihydroxypropyl group; a carbalkoxy group, for example, a β-carbo-(methoxy-, ethoxy- or propoxy)-ethyl group (in which the terminal alkyl group in ω'-position can carry a cyano, carbalkoxy, acyloxy or alkoxy group) or a β- or γ-carbo(methoxy- or ethoxy)-propyl group; an acylaminoalkyl group; for example, a β-(acetyl- or formyl)-aminoethyl group; an acyloxyalkyl group, for example, a β-acetyloxyethyl or β,γ-diacetoxypropyl group; a β-alkylsulphonylalkyl group, for example, a β-methanesulphonylethyl ethyl or β-ethanesulphonylethyl group; an alkyl- or arylcarbamoyloxyalkyl group, for example, a β-methylcarbamyloxyethyl group; an alkyloxycarbonyloxyalkyl group, for example, a β-(methoxy-, ethoxy- or isopropyloxy)-carbonyloxyethyl, γ-acetamidopropyl, β-(β'-acetylethoxycarbonyl)-ethyl, β-[β'-(cyano-, hydroxy-, methoxy- or acetoxy)-ethoxycarbonyl]-ethyl, cyanoalkoxyalkyl, β-carboxyethyl, β-acetylethyl, β-diethylaminoethyl, β-cyanoacetoxyethyl, β-benzoyloxyethyl or β-(para-alkoxy- or phenoxybenzoyloxy)-ethyl group. The groups $R_1$ and $R_2$ generally contain not more than 8, preferably not more than 5, carbon atoms. The residue c is preferably in ortho-position to the vinylidene group.

Specially preferred are those styryl dyestuffs that contain an alkyl substituent in ortho-position to the vinylidene group on the phenylene ring.

The following are given as examples of alkylene residues $R_2'$ (the terminal amino group of the azo dyestuff is included to indicate the position):

—NR₁'—C₂H₄—

—NR₁'—CH₂CH₂CH₂—

—NR₁'—C₂H₄—O—C₂H₄—

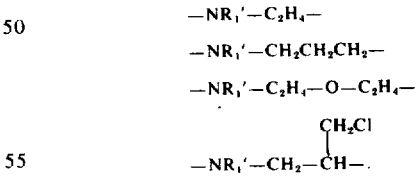

The residue X is, for example, a group corresponding to one of the following formulae (the group -C(CN)= is included to indicate the position):

—O—CO—C(CN)=

—NH—CO—C(CN)=

—N(CH₃)—CO—C(CN)=

—N(CH₂C₅H₆)—C(CN)=

—N—(alkyl)—CO—C(CN)—

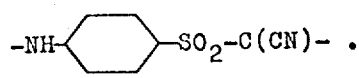

The introduction of the residue X may be effected by condensation, for example, by transesterification of a styryl dyestuff ester with a coupling component that contains a β-hydroxyethyl group attached to the nitrogen atom.

The diazo residue D is derived primarily from monocyclic or bicyclic amines of the formula D-NH, for example, any diazotizable amines that are free from substituents imparting solubility in water, but especially amines that contain a heterocyclic 5-membered ring having 2 or 3 hetero atoms, especially a nitrogen and one or two sulphur, oxygen or nitrogen atoms, and aminobenzenes, especially negatively substituted aminobenzenes, particularly those of the formula

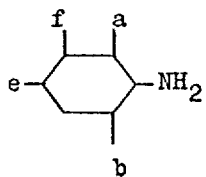

in which a represents a hydrogen or a halogen atom or an alkyl, alkoxy, nitro, cyano, carbalkoxy or alkylsulphone group, b represents a hydrogen or a halogen atom or an alkyl, cyano or trifluoromethyl group, e represents a nitro, cyano, carbalkoxy or alkylsulphonyl group or a halogen atom and f represents a hydrogen or halogen atom or carbalkoxy or a carboxylic acid amide group.

The following are given as examples: 2-aminothiazole, 2-amino-5-nitrothiazole, 2-amino-5-methylsulphonylthiazole, 2-amino-5-cyanothiazole, 2-amino-4-methyl-5-nitrothiazole, 2-amino-4-methylthiazole, 2-amino-4-phenylthiazole, 2-amino-4-(4'-chloro)-phenylthiazole, 2-amino-4-(4'-nitro)-phenylthiazole, 3-aminopyridine, 3-aminoquinoline, 3-aminopyrazole, 3-amino-1-phenylpyrazole, 3-aminoindazole, 3-amino-1,2,4-triazole, 5-(methyl-, ethyl-, phenyl- or benzyl)-1,2,4-triazole, 3-amino-1-(4'-methoxyphenyl)-pyrazole, 2-aminobenzthiazole, 2-amino-6-methyl-benzthiazole, 2-amino-6-methoxybenzthiazole, 2-amino-6-chlorobenzthiazole, 2-amino-6-cyanobenzthiazole, 2-amino-6-thiocyanobenzthiazole, 2-amino-6-nitrobenzthiazole, 2-amino-6-carboethoxybenzthiazole, 2-amino-(4- or 6)-methylsulphonylbenzthiazole, 2-amino-1,3,4-thiadiazole, 2-amino-1,3,5-thiadiazole, 2-amino-4-phenyl- or -4-methyl-1,3,5-thiadiazole, 2-amino-5-phenyl-1,3,4-thiadiazole, 2-amino-3-nitro-5-methylsulphonylthiophene, 2-amino-3,5-bis(methylsulphonyl)-thiophene, 5-amino-3-methylisothiazole, 2-amino-4-cyanopyrazole, 2-(4'-nitrophenyl)-3-amino-4-cyanopyrazole, 3- or 4-aminophthalimide, aminobenzene, 1-amino-2-trifluoromethyl-4-chlorobenzene, 1-amino-2-cyano-4-chlorobenzene, 1-amino-2-carbomethoxy-4-chlorobenzene, 1-amino-2-carbomethoxy-4-nitrobenzene, 1-amino-2-chloro-4-cyanobenzene, 1-amino-2-chloro-4-nitrobenzene, 1-amino-2-bromo-4-nitrobenzene, 1-amino-2-chloro-4-carbethoxybenzene, 1-amino-2-chloro-4-methylsulphonylbenzene, 1-amino-2-methylsulphonyl-4-chlorobenzene, 1-amino-2,4-dinitro-6-methylsulphonylbenzene, 1-amino-2,4-dinitro-6-(2'-hydroxyethylsulphonyl)benzene, 1-amino-2,4-dinitro-6-(2'-chloroethylsulphonyl)benzene, 1-amino-2-methylsulphonyl-4-nitrobenzene, 1-amino-2-methylsulphinyl-4-nitrobenzene, 1-amino-2,4-dinitrobenzene, 1-amino-2,4-dicyanobenzene, 1-amino-2-cyano-4-methylsulphonylbenzene, 1-amino-2,6-dichloro-4-cyanobenzene, 1-amino-2,6-dichloro-4-nitrobenzene, 1-amino-2,4-dicyano-6-chlorobenzene, 4-aminobenzoic acid cyclohexyl ester, 1-amino-2,4-dinitro-6-chlorobenzene and especially 1-amino-2-cyano-4-nitrobenzene, also 1-amino-benzene-2-, -3- or -4-sulphonic acid amides, for example, N-methyl- or N,N-dimethyl- or -diethyl amide, N,γ-isopropyloxypropyl-2-aminonaphthalene-6-sulphonic acid amide, N,γ-isopropyloxypropyl-1-aminobenzene-2-, -3- or -4-sulphonic acid amide, N-isopropyl-1-aminobenzene-2-, -3- or -4-sulphonic acid amide, N,γ-methoxypropyl-1-aminobenzene-2-, -3- or -4-sulphonic acid amide, N,N-bis(β-hydroxyethyl)-1-aminobenzene-2-, -3- or -4-sulphonic acid amide, 1-amino-4-chlorobenzene-2-sulphonic acid amide and the N-substituted derivatives thereof, 2-, 3- or 4-aminophenylsulphamate, 2-amino-4-, -5- or -6-methylphenylsulphamate, 2-amino-5-methoxyphenylsulphamate, 3-amino-6-chlorophenylsulphamate, 3-amino-2,6-dichlorophenylsulphamate, 4-amino-2- or -3-methoxyphenylsulphamate, N,N-dimethyl-2-aminophenylsulphamate, N,N-di-n-butyl-2-aminophenylsulphamate, N,N-dimethyl-2-amino-4-chlorophenylsulphamate, N,n-propyl-3-aminophenylsulphamate, N,N-di-n-butyl-3-aminophenylsulphamate, O(3-aminophenyl)-N-morpholine-N-sulphonate, O(3-aminophenyl)-N-piperidine-sulphonate, N-cyclohexyl-O-(3-aminophenyl)sulphamate, N(N-methylaniline)-O-(3-aminophenyl)sulphonate, N,N-diethyl-3-amino-6-methylphenyl-sulphamate, N-ethyleneimine-O-(4-aminophenyl)-sulphonate, N,N-dimethyl-4-aminophenylsulphamate, O-(n-propyl)-O-(3-aminophenyl)sulphonate, O,β-chloroethyl-O-(2-aminophenyl)sulphonate, O-benzyl-O-(3-aminophenyl)sulphonate, O-ethyl-O-(4-amino-2,6-dimethylphenyl)sulphonate, 4-aminoazobenzene, 3,2'-dimethyl-4-aminoazobenzene, 2-methyl-5-methoxy-aminoazobenzene, 4-amino-2-nitroazobenzene, 2,5-dimethoxy-4-aminoazobenzene, 4'-methoxy-4-aminoazobenzene, 2-methyl-4'-methoxy-4-aminoazobenzene, 3,6,4'-trimethoxy-4-aminoazobenzene, 4'-chloro-4-aminoazobenzene, 2'- or 3'-chloro-4-aminoazobenzene, 3-nitro-4-amino-2',4'-dichloroazobenzene and 4-aminoazobenzene-4'-sulphonic acid amide.

Instead of the above-mentioned diazo components free from ionic groups imparting solubility in water, those containing fibre-reactive groups may also be used, for example, s-triazinyl residues carrying 1 or 2 chlorine or bromine atoms on the triazine ring, pyrimidyl residues carrying 1 or 2 chlorine atoms or 1 or 2 arylsulphonyl or alkanesulphonyl groups on the pyrimidine ring, mono- or bis-(γ-halogeno-β-hydroxypropyl)-amino groups, β-halogenoethylsulphamyl residues, β-halogenoethoxy groups, β-halogenoethylmercapto groups, 2-chlorobenzthiazolyl-6-azo groups, 2-chlorobenzthiazolyl-6-amino groups, γ-halogen-β-hydroxypropylsulphamyl residues, chloroacetylamino groups, α,β-dibromopropionyl groups, vinylsulphonyl groups and 2,3-epoxypropyl groups.

The following are examples of suitable fibrereactive diazo components: N,β-chloroethyl-3-chloro-4-aminobenzene sulphamide (hydrochloride), N,β-chloroethyl-4-aminobenzene sulphamide (hydrochloride), 3- bromo-4-amino-ω-chloroacetophenone, N,γ-chloro-β-hydroxypropyl-4-aminobenzene sulphamide, N,β-chloroethyl-1-amino-4-naphthylsulphonamide, N,β-chloroethyl-1-amino-3,5-dichlorobenzenesulphamide and 4-(γ-chloro-β-hydroxypropoxy)-aniline.

The diazotization of the above-mentioned diazo components can be effected, for example, with a mineral acid and sodium nitrite or, for example, with a solution of nitrosylsulphuric acid in concentrated sulphuric acid, depending on the position of the amino group concerned.

Coupling can be carried out in known manner, for example, in a neutral to acid medium, if necessary, in the presence of sodium acetate or a similar buffer that influences the rate of coupling, or a catalyst, for example, dimethylformamide or pyridine, or the salts thereof.

The dyestuffs can also be manufactured by reacting two dyestuff molecules (A) and (B) of the formulae (A)     

(B)     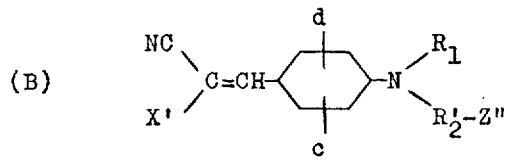

in which D, B, R$_1$, R$_2'$, d and c have the meanings given above, X' = —CN, —SO$_2$-aryl, —COHN$_2$ or —CO—O-alkyl, Z' = —OH, —NH$_2$, -SH or —NH-alkyl and Z" = a reactive halogen atom, —O-CO—Cl, —O—CO-alkylene—O—COCL or —O—CO-alkylene-CO—Cl.

In this manner the dyestuffs of the formula

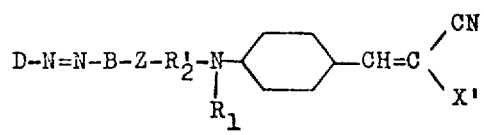

are obtained, in which Z represents a divalent organic residue or an oxygen atom or an —NH— group, preferably, a residue of the formula -O-CO-alkylene-CO-O or —O—CO—O—.

Those representatives of the above-mentioned heterocyclic diazo components that contain a quaternatable nitrogen atom can also be coupled by oxidation in the N-alkylated form as hydrazones or as azosulphones (cf. Angewandte Chemie, Volume 70, 215 [1958]; Volume 74, 818 [1962]; Volume 80, 343 [1968]).

Those representatives of the new dyestuffs that contain a quaternated amino group can also be obtained by quaternating the corresponding dyestuffs that contain a non-quaternated amino group by treating with alkylating agents.

Examples of suitable alkylating or quaternating agents are as follows: esters of strong mineral acids or organic sulphonic acids, for example, dimethyl sulphate, diethyl sulphate, alkyl halides, for example, methyl chloride, methyl bromide or methyl iodide, aralkyl halides, for example, benzyl chloride, esters of low-molecular alkane sulphonic acids, for example, methyl esters of methane-, ethane- or butane-sulphonic acid, and esters of benzene-sulphonic acids that can contain additional substituents, for example, methyl-, ethyl- propyl- or butyl-esters of benzene sulphonic acid, of 2- or 4-methylbenzene sulphonic acid, 4-chlorobenzene sulphonic acid or 3- or 4-nitrobenzene sulphonic acid.

It is expedient to effect alkylation by heating in an inert organic solvent, for example, a hydrocarbon, for example, benzene, toluene or xylene, a halogenated hydrocarbon, for example, carbon tetrachloride, tetrachloroethane, chlorobenzene or ortho-dichlorobenzene, or a nitrohydrocarbon, for example, nitromethane, nitrobenzene or a nitronaphthalene. Acid anhydrides, acid amides or nitriles, for example, acetic anhydride, dimethylformamide or acetonitrile or also dimethyl sulphoxide can also be used as solvents in the alkylation process. Instead of a solvent, a large excess of alkylating agent may also be used. In this case, care must be taken to ensure that the mixture is not unduly heated, since the reaction is strongly exothermic. It is nevertheless necessary in most cases, especially in the presence of organic solvents, to heat the reaction mixture externally in order to initiate the reaction. In special cases, the alkylation can also be carried out in an aqueous medium or with the use of an alcohol, if necessary, in the presence of a small amount of potassium iodide.

Should it be necessary, purification of the dyestuff salts is advantageously effected by dissolution in water, any unreacted starting dyestuff being removed by filtration in the form of insoluble residue. The dyestuff can be reprecipitated from the aqueous solution by the addition of a water-soluble salt, for example, sodium chloride.

The non-quaternated dyestuffs are generally insoluble in water.

The new dyestuffs, mixtures thereof, and mixtures of the new dyestuffs with other azo dyestuffs are eminently suitable for dyeing and printing leather, wool and silk and especially synthetic fibres, for example, acrylic or acrylonitrile fibres, polyacrylonitrile fibres and copolymers of acrylonitrile and other vinyl compounds, for example, acrylic esters, acylamides, vinylpyridine, vinyl chloride or vinylidene chloride, copolymers of dicyanoethylene and vinyl acetate, and of acrylonitrile block-copolymers, polyurethane fibres, polyolefins, for example, basified, nickel-modified or unmodified polypropylene, cellulose triacetate and secondary acetate fibres and especially polyamide fibres, for example, nylon 6, nylon 6.6 or nylon 12, and also fibres made from aromatic polyesters, for example, terephthalic acid and ethylene glycol or 1,4-dimethylcyclohexane, and copolymers of terephthalic and isophthalic acid and ethylene glycol.

For dyeing in an aqueous liquor, the water-insoluble dyestuffs are advantageously used in a finely divided form and dyeing is carried out in the presence of a dispersing agent, for example, sulphite cellulose waste liquor, or a synthetic detergent, or a combination of different wetting and dispersing agents. Prior to dyeing, it is generally advantageous to convert the dyestuff into a dyeing preparation that contains a dispersing agent and the dyestuff in a form such that a fine dispersion is obtained when the preparation is diluted with water. Such dyestuff preparations may be obtained in known manner, for example, by grinding the dyestuff in the dry or wet state in the presence or absence of a dispersing agent.

To obtain stronger dyeings on polyethylene terephthalate fibres it is generally advantageous to add a swelling agent to the dyebath, or more especially to carry out the dyeing process under superatmospheric pressure at a temperature above 100°C, for example, at 120°C. Suitable swelling agents are aromatic carboxylic acids, for example, benzoic acid and salicyclic acid; phenols, for example, ortho- or para-hydroxydiphenyl; aromatic halogen compounds, for example, ortho-dichlorobenzene or diphenyl.

For thermofixation of the dyestuff, the padded polyester fabric is heated to a temperature above 100°C, for example, to a temperature between 180 and 210°C, advantageously after drying, for example, in a current of warm air.

The dyeings obtained in accordance with the present process can be subjected to an after-treatment, for example, by heating with an aqueous solution of a non-ionic detergent.

The dyestuffs may also be applied by printing processes. In this method of application a printing paste is used that contains, for example, the finely dispersed dyestuff and the usual printing adjuvants, for example, wetting and thickening agents.

Furthermore, dyeing can also be carried out in a dyebath containing an organic solvent, for example, a mixture of perchloroethylene and dimethylformamide.

The above-mentioned processes yield strong dyeings and prints possessing good properties of fastness.

The new water-insoluble dyestuffs can also be used in the spin-coloration of polyamides, polyesters and polyolefins. The polymer to be coloured is advantageously in the form of a powder, grains or chips, in the form of a spinning solution or in the molten state when mixed with the dyestuff, the latter being either in the dry state or in the form of a dispersion or solution in a solvent that may be volatile. The dyestuff is homogeneously dispersed in the polymer solution or melt and the mixture is then processed into fibres, yarns, monofilaments, films, and so forth, in known manner by casting, compression moulding or extrusion.

The following Examples illustrate the invention, the parts and percentages being by weight, unless otherwise stated.

EXAMPLE 1

47.5 Parts of N-β-cyanoethyl-N-β-hydroxyethylaniline and 42.6 parts of cyanoacetic acid are refluxed for 16 hours with 100 parts of benzene in a water separator during which 4.3 parts of water, corresponding to a yield of 95 %, are separated. The residue is diluted with benzene and the excess of cyanoacetic acid is washed out with water in a separating funnel. The benzene phase is dried and evaporated. 58 Grams (90 % of the theoretical yield) of the cyanoacetic ester remain behind in the form of a yellowish, thick oil corresponding to the formula

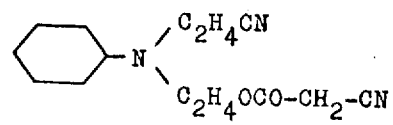

30 Parts of 3-chloro-N,N-bis-β-acetoxyethylaniline are introduced into 31 parts by volume of dimethylformamide. 10.6 Parts by volume of $POCl_3$ are added dropwise at 15 to 20°C, the batch is stirred for 30 minutes at 15° to 20°C, then for 1½ hours at 90°C, discharged hot into a solution of 48 parts by volume of NaOH (conc.) in 500 parts of water, and the batch is rendered neutral. The yellowish product that precipitates is isolated and washed with water. After drying, 31 parts (94 % of the theoretical yield) of the aldehyde of the formula

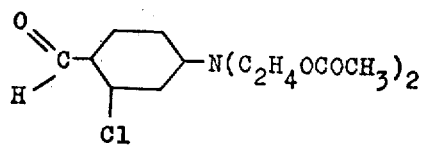

are obtained.

6.6 Parts of this aldehyde are condensed with 5.2 parts of the amine of the formula given above in 30 parts by volume of dioxane with the addition of catalytic amounts of piperidine. The batch is refluxed for 4 hours while stirring, the dioxane is removed by distillation and the coupling component is obtained in the form of an orange-red oil; it corresponds to the formula

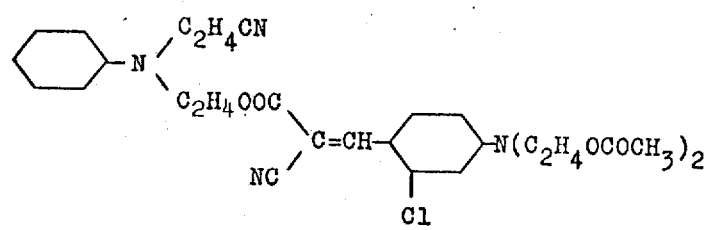

1.8 Parts of 2-chloro-4-nitroaniline are diazotized in the usual manner with 1N nitrosylsulphuric acid, and the product is discharged at 0° to 10° into 140 parts by volume of a 6:1 mixture of acetic acid and propionic acid. A solution of 5.7 parts of the coupling component of the above formula in 70 parts by volume of the acid mixture specified above is added dropwise to the solution of 0° to 10°C, the batch is stirred for one hour at 0° to 10°C, 100 parts of water are slowly added dropwise at that temperature, the batch is stirred overnight at 0° to 10°C, the precipitate that forms is isolated by powerful vacuum filtration and washed with water until the washings run neutral. The residue is dried and 5 parts (67 % of the theoretical yield) of the styryl-azo dyestuff of the formula

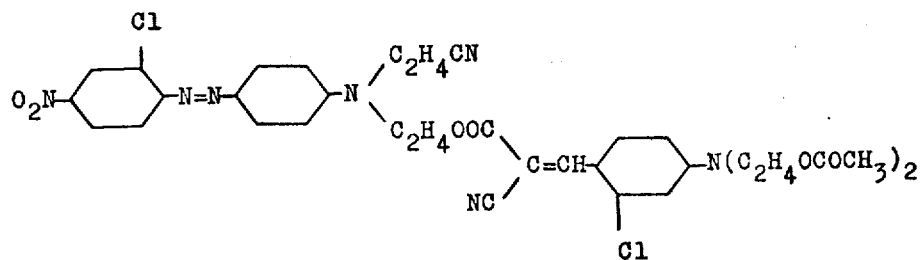

are obtained. It dyes polyester fibres an orange shade possessing excellent fastness to light and the maximum degree of fastness to sublimation.

The following Table 1 lists components from which further styrylazo dyestuffs may be obtained by condensing the cyanoacetic ester specified above with an aldehyde listed in Column I in the manner described and coupling with a diazonium compound of a diazo component listed in Column II. The shade that the styryl-azo dyestuff so obtained yields on polyester is indicated in Column III.

Table 1

| | I | II | III |
|---|---|---|---|
| 1 | O=C(H)-C₆H₃(CH₃)-N(C₂H₅)(C₂H₄OCO-C₆H₅) | O₂N-C₆H₃(Cl)-NH₂ | orange |
| 2 | O=C(H)-C₆H₄-N(C₂H₅)(C₂H₄CN) | — " — | — " — |
| 3 | O=C(H)-C₆H₃(CH₃)-N(C₂H₅)(C₂H₄CN) | — " — | — " — |
| 4 | O=C(H)-C₆H₄-N(C₂H₄CN)(C₂H₄OCH₃) | — " — | — " — |
| 5 | O=C(H)-C₆H₄-N(C₂H₄CN)(C₂H₄OCOCH₃) | — " — | — " — |
| 6 | O=C(H)-C₆H₄-N(C₂H₄OCOCH₃)₂ | O₂N-C₆H₃(CN)-NH₂ | yellowish-red |
| 7 | O=C(H)-C₆H₃(CH₃)-N(C₂H₅)(C₂H₄OCO-C₆H₅) | O₂N-C₆H₃(CN)-NH₂ | — " — |
| 8 | O=C(H)-C₆H₄-N(C₂H₄OCOCH₃)₂ | — " — | — " — |
| 9 | O=C(H)-C₆H₄-N(C₂H₅)(C₂H₄CN) | — " — | — " — |

Table 1 – Continued

| | I | II | III |
|---|---|---|---|
| 10 | $\underset{H}{O=}C-\underset{CH_3}{\bigcirc}-N\underset{C_2H_4CN}{\overset{C_2H_5}{<}}$ | $O_2N-\underset{NH_2}{\overset{CN}{\bigcirc}}$ | yellowish-red |
| 11 | $\underset{H}{O=}C-\underset{Cl}{\bigcirc}-N(C_2H_4OCOCH_3)_2$ | – " – | – " – |
| 12 | $\underset{H}{O=}C-\bigcirc-N\underset{C_2H_4OCH_3}{\overset{C_2H_4CN}{<}}$ | – " – | – " – |
| 13 | $\underset{H}{O=}C-\bigcirc-N\underset{C_2H_4OCOCH_3}{\overset{C_2H_4CN}{<}}$ | – " – | – " – |
| 14 | $\underset{H}{O=}C-\bigcirc-N(C_2H_4CN)_2$ | $O_2N-\underset{Cl}{\overset{Cl}{\bigcirc}}-NH_2$ | yellowish-brown |
| 15 | $\underset{H}{O=}C-\bigcirc-N\underset{C_2H_4S-\bigcirc-Cl}{\overset{C_2H_5}{<}}$ | $CH_3O_2S-\underset{Cl}{\bigcirc}-NH_2$ | yellowish-orange |
| 16 | $\underset{H}{O=}C-\bigcirc-N\underset{C_2H_4-O-\bigcirc}{\overset{C_2H_5}{<}}$ | $Cl-\underset{CN}{\bigcirc}-NH_2$ | yellowish-orange |
| 17 | $\underset{H}{O=}C-\underset{CH_3}{\bigcirc}-N\underset{C_2H_4OC_2H_4CN}{\overset{C_2H_5}{<}}$ | $H_5C_2O-\bigcirc\underset{S}{\overset{N}{>}}C-NH_2$ | orange-red |
| 18 | $\underset{H}{O=}C-\bigcirc-N\underset{C_2H_4OCO-C\underset{S}{\overset{HC=CH}{>}}C-COOCH_3}{\overset{C_2H_5}{<}}$ | $O_2N-C\underset{S}{\overset{HC=N}{>}}C-NH_2$ | red |
| 19 | $\underset{H}{O=}C-\bigcirc-N\underset{C_2H_4OCOCH_3}{\overset{CH_2-\bigcirc}{<}}$ | $O_2N-C\underset{S}{\overset{HC=N}{>}}C-NH_2$ | red |
| 20 | $\underset{H}{O=}C-\bigcirc-N\underset{C_2H_4OCO-\bigcirc-COOCH_3}{\overset{C_3H_6}{<}}$ | $O_2N-\underset{COOCH_3}{\bigcirc}-NH_2$ | orange |
| 21 | $\underset{N}{O=}C-\bigcirc-N\underset{C_2H_4OCONH-\bigcirc}{\overset{C_2H_5}{<}}$ | – " – | – " – |
| 22 | $\underset{H}{O=}C-\underset{CH_3}{\bigcirc}-N(C_2H_4Cl)_2$ | – " – | – " – |

Table I – Continued

| | I | II | III |
|---|---|---|---|
| 23 | OHC-C6H4-N(C4H9)(C2H4Cl) | O2N-C6H3(SO2CH3)-NH2 | yellowish-red |
| 24 | OHC-C6H3(CH3)-N(C2H5)(C2H4OH) | — " — | — " — |
| 25 | OHC-C6H3(CH3)-N(C2H4OH)2 | O2N-C6H3(SO2CH3)-NH2 | — " — |
| 26 | OHC-C6H4-N(C2H4OCO-C6H4-OCH3)2 | O2N-C6H2(CN)(Br)-NH2 | red |
| 27 | OHC-C6H3(CH3)-N(C2H4OCOCH3)(CH2-CH2-CH2) | O2N-C6H2(NO2)(Cl)-NH2 | red |
| 28 | OHC-C6H4-N(C2H4-COOCH3)(C2H5) | O2N-C6H3(CN)-NH2 | yellowish-red |
| 29 | OHC-C6H4-N(C2H4-OCO-OCH3)(C2H5) | O2N-C6H2(Cl)(Cl)-NH2 | yellowish-brown |
| 30 | OHC-C6H4-N(C2H4-OCO-NH-C2H5)(C2H5) | O2N-(thiazole)-NH2 | red |
| 31 | OHC-C6H4-N(C3H6NH-CO-NHC2H5)(C2H5) | Cl-C6H3(CN)-NH2 | yellowish-orange |
| 32 | OHC-C6H4-N(C2H4-COOCH3)(C2H4-O-COCH3) | Cl-C6H2(Cl)(Br)-NH2 | — " — |
| 33 | OHC-C6H4-N(C2H4-O-CO-CH3)2 | O2N-(benzothiazole)(NH2)(Br) | greenish-blue |

The following Table 2 lists components from which further dyestuffs can be obtained by condensing the aldehyde of the formula

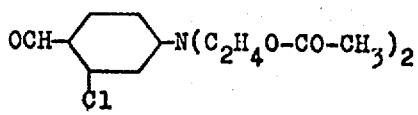

with a compound listed in Column I and then coupling with a diazo compound of an amine listed in Column II. The shade obtained on polyester is listed in Column III.

EXAMPLE 2

2.3 Parts of para-amino-ω-(N-chlorotrimethylamino)-acetophenone are dissolved in 50 parts of N hydrochloric acid, the solution is cooled to 0°C and diazotized with 4N sodium nitrite solution. The diazo solution is added dropwise to a solution of 4.3 parts of the coupling component described in Example 1 dissolved in 70 parts by volume of acetone. The batch is stirred for some time, the dyestuff is salted out with sodium chloride, isolated by filtration and dried in vacuo. A product of the formula

| | I | II | III |
|---|---|---|---|
| 1 | phenyl-N(C$_4$H$_9$)(C$_2$H$_4$OCO-CH$_2$-CN), CH$_3$ substituent | O$_2$N—C$_6$H$_3$(CN)—NH$_2$ | red |
| 2 | phenyl-N(C$_2$H$_4$OCOCH$_3$)$_2$, NHCO-CH$_2$-CN | O$_2$N—C$_6$H$_4$—NH$_2$ | orange |
| 3 | phenyl-N(C$_2$H$_4$CN)$_2$, NHCO-CH$_2$-CN | O$_2$N—C$_6$H$_3$(Cl)—NH$_2$ | — " — |
| 4 | phenyl-N(C$_2$H$_4$CN)(C$_2$H$_4$OCO-CH$_2$-CN), Cl substituent | C$_6$H$_5$-C=N, N-S-C-NH$_2$ (thiadiazole) | — " — |
| 5 | phenyl-N(C$_2$H$_4$CN)(C$_2$H$_4$OCO-CH$_2$-CN), CH$_3$ substituent | O$_2$N—C$_6$H$_3$(CN)—NH$_2$ | yellowish-red |
| 6 | phenyl-N(C$_2$H$_4$OC$_2$H$_4$CN)(C$_2$H$_4$OCO-CH$_2$-CN), CH$_3$ substituent | Cl—C$_6$H$_3$(CF$_3$)—NH$_2$ | yellowish-red |
| 7 | phenyl-N(C$_2$H$_5$)(C$_2$H$_4$OCO-CH$_2$-CN), OCH$_3$ substituent | — " — | — " — |
| 8 | phenyl-N(C$_2$H$_4$CN)(CH OCO-CH$_2$-CN) | O$_2$N—C$_6$H$_3$(Cl)—NH$_2$ | orange |
| 9 | phenyl-N(CH$_2$-phenyl)(C$_2$H$_4$OCO-CH$_2$-CN), NHCO-C$_6$H$_3$(Cl)(Cl) substituent | O$_2$N—C$_6$H$_4$—NH$_2$ | — " — |

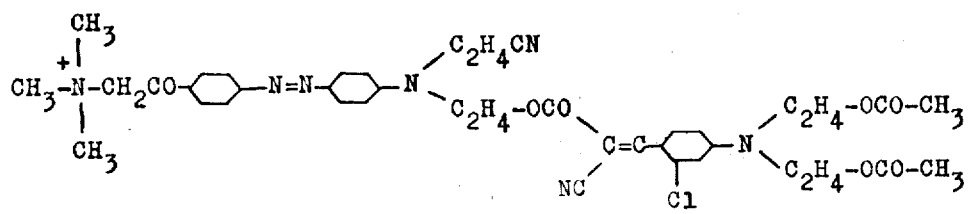

is obtained with dyes polyacrylonitrile fibres a yellow shade.

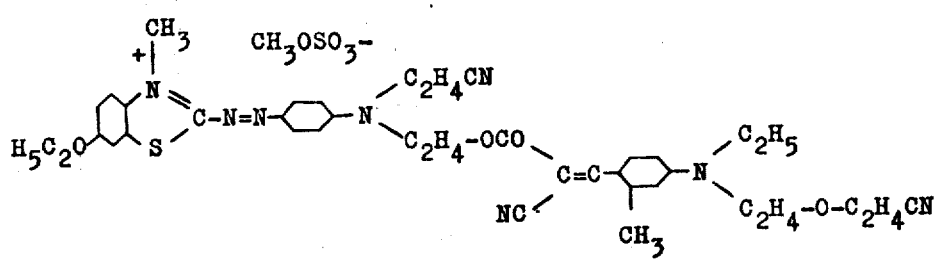

EXAMPLE 3

7 Parts of dyestuff No. 17 listed in Table 1 are heated to about 80°C in 70 parts of the dimethylformamide, and 2 parts of dimethyl sulphate are added. The batch is stirred at the same temperature until the dyestuff is fully quaternated. The product so obtained is precipitated by the addition of ethyl acetate, isolated, and dried in vacuo. A dyestuff of the formula is obtained that dyes polyacrylonitrile fibres a bluish green shade.

The dyestuffs listed below are obtained in an analogous manner and dye polyacrylonitrile fibres the shades indicated:-

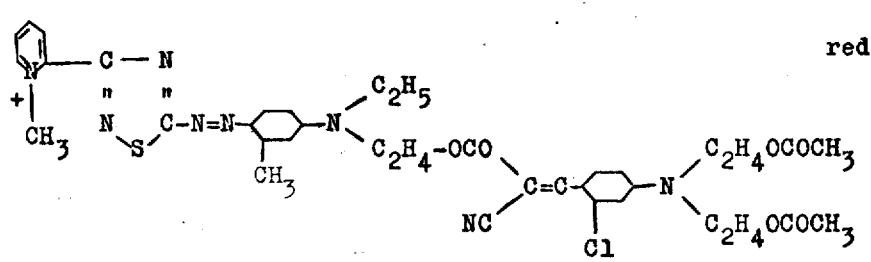

red

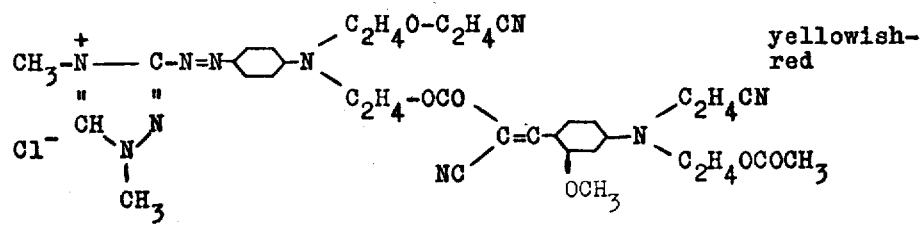

yellowish-red

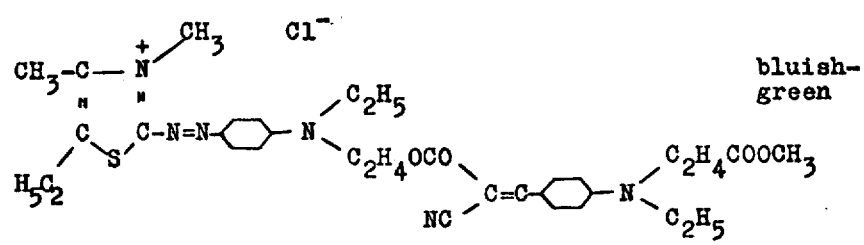

bluish-green

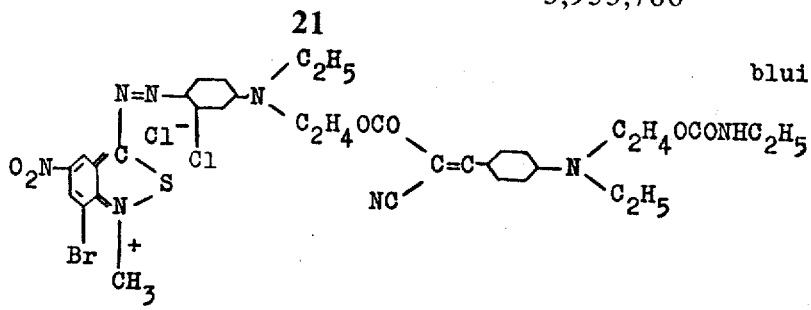

bluish-green

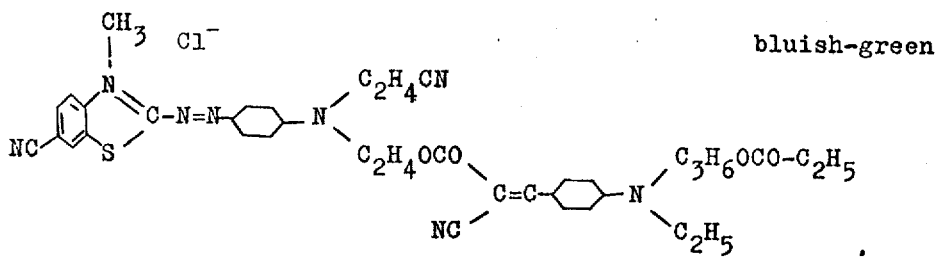

bluish-green

We claim:
1. A dyestuff of the formula

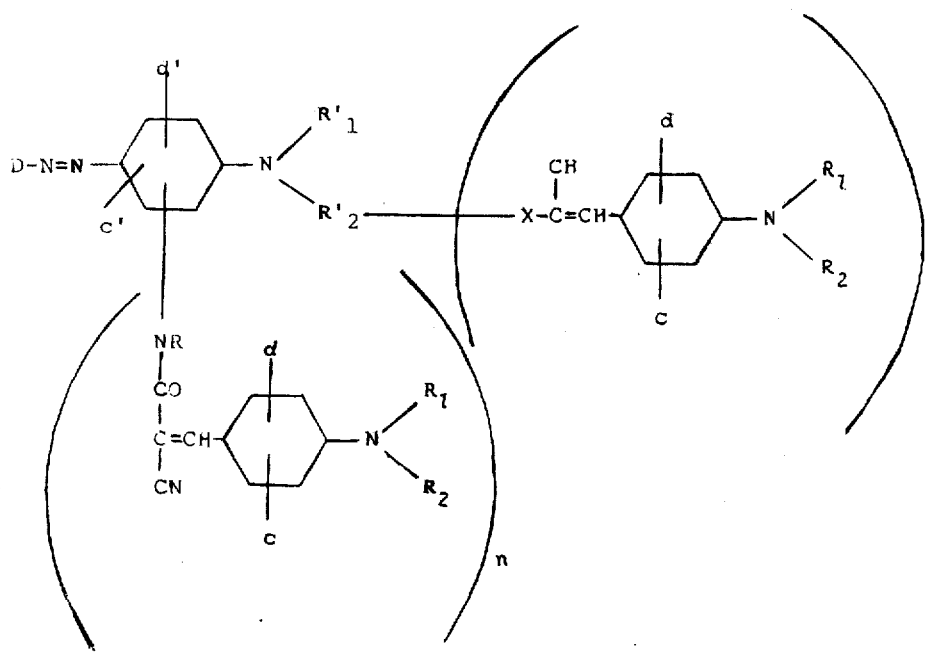

wherein
X is - phenylene — $SO_2$—, [—OCO—N($CH_2C_6H_5$)—CO-] —OCO—, —N($CH_2C_6H_5$)— or -N($C_1$-$C_2$-alkyl)—OC—;

c, d and d' each is hydrogen, chlorine, $C_1$-$C_2$ alkyl, $C_1$-$C_2$ alkoxy, phenyl, phenoxy or phenylthio;

c' is the same as c, d or d' or is bromine, trifluoromethyl [$C_{1-10}$-hydrocarbylcarbonylamino, $C_1$-$C_6$ hydrocarbylsulfonylamino, $C_1$-$C_8$-hydrocarbyloxycarbonylamino or $C_1$-$C_8$ -hydrocarbylaminocarbonylamino,]acylamino- or N-methyl-acylamino wherein acyl represents formyl, acetyl, propionyl, butyryl, benzoyl, methylsulfonyl, ethylsulfonyl, p-tolylsulfonyl, methoxycarbonyl, phenoxycarbonyl, aminocarbonyl or butylaminocarbonyl R is hydrogen or $C_1$-$C_2$ alkyl, $R_1$, $R_2$, $R'_1$ and $R'_2$ each are, independently $C_1$-$C_5$-alkyl or $C_2$-$C_5$ oxaalkyl and $C_1$-$C_5$-alkyl or $C_2$-$C_5$ oxaalkyl substituted by chlorine, fluorine, hydroxy, $C_1$-$C_5$ alkylcarbonyloxy cyano, bromine, phenyl, phenoxy, phenylmercapto, dichlorophenylmercapto, methoxycarbonyl-thienyl-2-carbonyloxy, benzoyloxy, methoxycarbonyl-benzoyloxy, methoxy-benzoyloxy, $C_1$-$C_5$-alkylaminocarbonyloxy, phenylaminocarbonyloxy, $C_1$-$C_5$-alkylaminocarbonylamino, $C_1$-$C_5$-alkoxycarbonyloxy or $C_1$-$C_5$-alkoxycarbonyl, m and n are each 0 or 1, not only of said m and n being zero at any one time, and with the proviso that when m is 1, $R°_2$ represents $C_2$-$C_4$ alkylene or $C_2$-$C_4$, oxaalkylene, said alkylene and oxaalkylene being unsubstituted or substituted by chloro, and D is selected from the group consisting or thiazolyl, thiadiazolyl, benzthiazolyl, isothiazolyl, pyrazolyl, indazolyl, pyridyl, quinolyl, benzisothiazolyl and triazolyl which is unsubstituted or substituted with one to three substituents selected from the group consisting of cyano lower alkyl, lower alkoxy, chloro, thiocyano, nitro, carbethoxy, methylsulphonyl, benzyl, phenyl, methoxyphenyl, chlorophenyl and pyridyl-(2); and the N-methyl chloride or N-methyl methylsulfate quaternary salt thereof.

2. A dyestuff of claim 1 of the formula

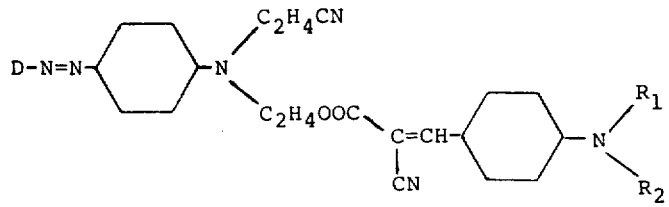

3. A dyestuff of claim 2 wherein D is

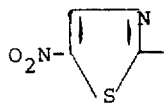

4. The dyestuff of claim 3 wherein $R_1$ is benzyl and $R_2$ is acetoxyethyl.

5. The dyestuff of claim 3 wherein $R_1$ is ethyl and $R_2$ is 5-methoxycarbonyl-thienyl-2-carbonyloxy.

6. The dyestuff of claim 3 wherein $R_1$ is ethylaminocarbonyloxyethyl and $R_2$ is ethyl.

7. The dyestuff of claim 2 wherein D is

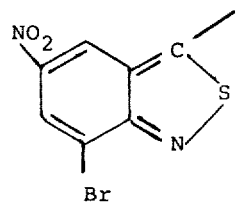

and $R_1$ and $R_2$ are acetoxyethyl.

8. The dyestuff of claim 1 of the formula

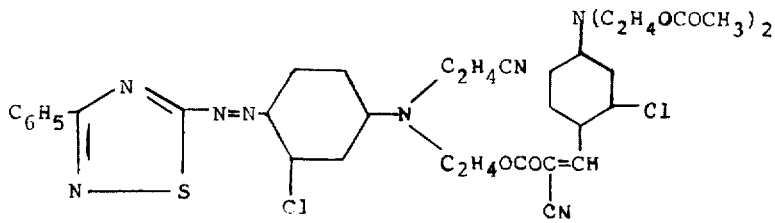

9. The dyestuff of claim 1 of the formula

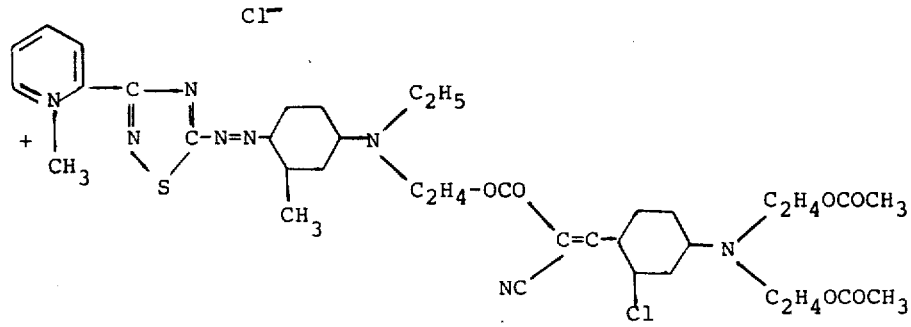

10. The dyestuff of claim 1 of the formula

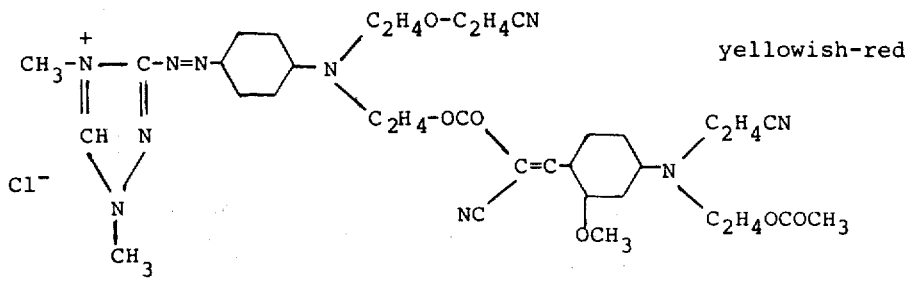

yellowish-red

11. The dyestuff of claim 1 of the formula
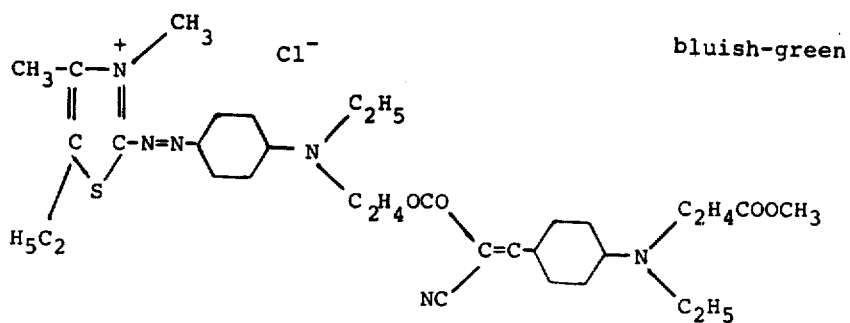
bluish-green
12. The dyestuff of claim 1 of the formula
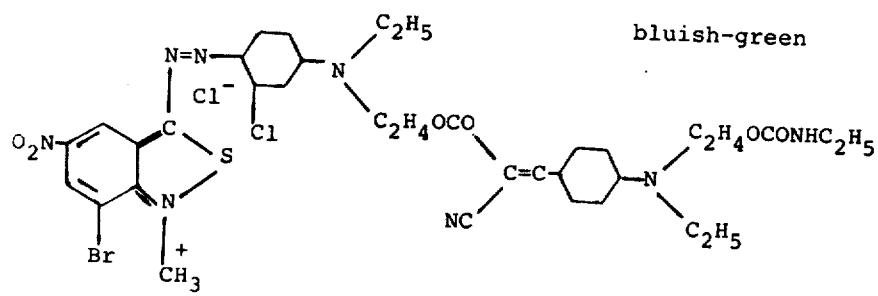
13. The dyestuff of claim 1 of the formula
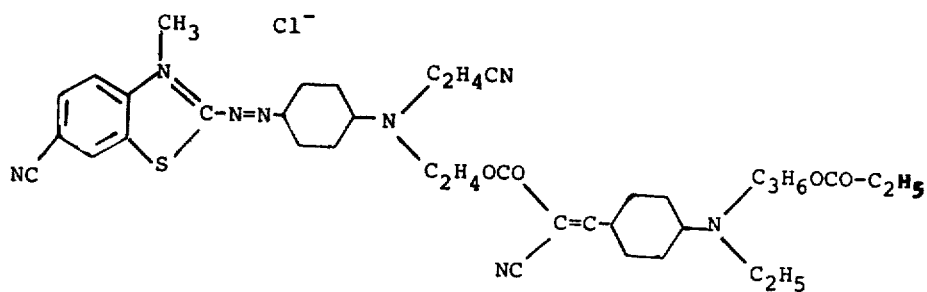
14. A dyestuff according to claim 1 of the formula
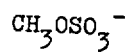
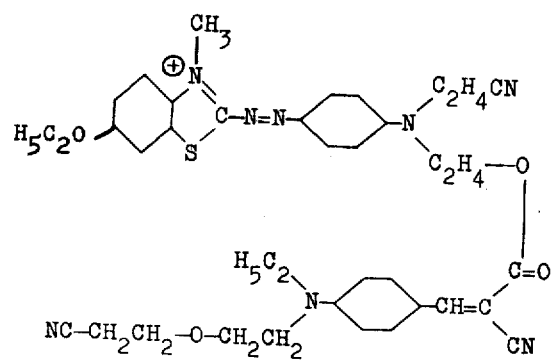
* * * * *

UNITED STATES PATENT AND TRADEMARK OFFICE
CERTIFICATE OF CORRECTION

PATENT NO. : 3,933,786
DATED : January 20, 1976
INVENTOR(S) : Peter et al.

It is certified that error appears in the above-identified patent and that said Letters Patent are hereby corrected as shown below:

Claim 1, structure on right-hand side of parenthesis, insert

-- m --;

lines 2 and 3 after structure, delete "[-OCO-N(CH$_2$C$_6$H$_5$-CO]";

lines 8-11, delete "[C$_{1-10}$-hydrocarbylcarbonylamino, C$_1$-C$_6$ hydrocarbylsulfonylamino, C$_1$-C$_8$ hydrocarbyloxycarbonylamino or C$_1$-C$_8$ hydrocarbylaminocarbonylamino,]

line 60 delete "not" and insert after only -- one --;

line 63, delete "R°$_2$" and insert -- R'$_2$ --;

Signed and Sealed this fifteenth Day of June 1976

[SEAL]

Attest:

RUTH C. MASON
Attesting Officer

C. MARSHALL DANN
Commissioner of Patents and Trademarks